United States Patent
Anderson et al.

(10) Patent No.: US 11,590,014 B2
(45) Date of Patent: *Feb. 28, 2023

(54) COMPRESSION APPARATUS FOR SYNOVIAL JOINTS AND METHODS OF USE THEREOF

(71) Applicant: HOTCOLD MOTION COMPRESS LLC, Glen Burnie, MD (US)

(72) Inventors: Clayton Anderson, Glen Burnie, MD (US); Danielle N. Anderson, Glen Burnie, MD (US)

(73) Assignee: HOTCOLD MOTION COMPRESS LLC, Glen Burnie, MD (US)

(*) Notice: Subject to any disclaimer, the term of this patent is extended or adjusted under 35 U.S.C. 154(b) by 283 days.

This patent is subject to a terminal disclaimer.

(21) Appl. No.: 16/549,672

(22) Filed: Aug. 23, 2019

(65) Prior Publication Data

US 2019/0374362 A1   Dec. 12, 2019

Related U.S. Application Data

(63) Continuation-in-part of application No. 15/146,420, filed on May 4, 2016, now Pat. No. 10,434,000.

(Continued)

(51) Int. Cl.
*A61F 5/01* (2006.01)
*A61F 7/02* (2006.01)
(Continued)

(52) U.S. Cl.
CPC .......... *A61F 5/0109* (2013.01); *A61F 5/0111* (2013.01); *A61F 5/0118* (2013.01);
(Continued)

(58) Field of Classification Search
CPC ........ A61F 5/0111; A61F 5/00; A61F 5/0127; A61F 13/066; A61F 5/0102; A61F 5/0585
See application file for complete search history.

(56) References Cited

U.S. PATENT DOCUMENTS 5,113,877 A * 5/1992 Johnson, Jr. .......... A61F 5/0111
                                                            128/869
5,445,603 A * 8/1995 Wilkerson ............ A61F 5/0127
                                                            602/23

(Continued)

*Primary Examiner* — Ophelia A Hawthorne
(74) *Attorney, Agent, or Firm* — Offit Kurman, P.A.; Joseph P. Mathew

(57) ABSTRACT

Disclosed herein is a compression apparatus useful in treating pain, inflammation, or other conditions of a joint and joint area through use of compression and optionally temperature control. The compression apparatus is configured for physical and functional flexibility in that the apparatus is flexible and can be worn over or under clothing. The compression apparatus is generally suited for support of an ankle joint, a knee joint, a wrist joint, shoulder joint, elbow joint or hip joint depending on size, shape and securement configurations. In one embodiment, the compression apparatus comprises at least one flexible compression member and at least one securement means configured for adjustably providing compression to the joint area of a wearer. In certain embodiments, an apparatus of the present disclosure may comprise temperature-control means, decorative features, devices for visual display of treatment information such as elevation and temperature, as well as other information useful in treatment.

4 Claims, 12 Drawing Sheets

Related U.S. Application Data

(60) Provisional application No. 62/156,390, filed on May 4, 2015.

(51) Int. Cl.
  *A61F 5/02* (2006.01)
  *A61F 7/10* (2006.01)

(52) U.S. Cl.
  CPC ............ *A61F 5/0193* (2013.01); *A61F 5/028* (2013.01); *A61F 7/02* (2013.01); *A61F 7/10* (2013.01); *A61F 2007/0219* (2013.01); *A61F 2007/108* (2013.01)

(56) References Cited

U.S. PATENT DOCUMENTS

| | | | | |
|---|---|---|---|---|
| 5,743,867 | A * | 4/1998 | Hickling | A61F 7/02 |
| | | | | 602/65 |
| 6,032,286 | A * | 3/2000 | Thomas | A61F 5/0111 |
| | | | | 128/892 |
| 6,503,218 | B1 * | 1/2003 | Ascheman | A61F 5/0111 |
| | | | | 602/23 |
| 10,434,000 | B2 * | 10/2019 | Anderson | A61F 5/0585 |
| 2007/0049855 | A1 * | 3/2007 | Mattear | A61F 5/30 |
| | | | | 602/27 |
| 2012/0203156 | A1 * | 8/2012 | Dar | A61N 1/36003 |
| | | | | 602/16 |
| 2013/0012855 | A1 * | 1/2013 | Giza | A61F 5/0111 |
| | | | | 602/27 |
| 2014/0316321 | A1 * | 10/2014 | Mueller | A61F 5/0111 |
| | | | | 602/27 |

\* cited by examiner

COMPRESSION APPARATUS FOR SYNOVIAL JOINTS AND METHODS OF USE THEREOF

CROSS REFERENCE TO RELATED APPLICATIONS

This application is a continuation-in-part of U.S. patent application Ser. No. 15/146,420, filed May 4, 2016, which in turn claims priority to earlier filed U.S. Provisional Patent Application No. 62/156,390, filed on May 4, 2015, the contents of which are herein incorporated by reference in their entirety.

STATEMENT REGARDING FEDERALLY SPONSORED RESEARCH AND DEVELOPMENT

This invention was made in its entirety without federal funding.

BACKGROUND OF THE INVENTION

For injuries to joints, especially synovial joints, rest, ice or heat are typically an integral part of recovery. In a busy lifestyle it is difficult to stay stationary often enough and long enough to thoroughly ice or heat an injured joint area as prescribed. In many cases, patients are limited to ice or heat treatments when they have an opportunity to remain stationary. Time spent waiting for a period of relative immobility represents one or more missed opportunities for a person suffering from a joint injury to administer ice or heat or rest the joint. The shortening of ice and heat rehabilitation sessions can also significantly lengthen a patient's recovery time. Thus, there is a need in the art for a solution that allows a patient suffering from a joint injury the opportunity to ice or heat the injured joint even while on the move.

SUMMARY OF THE INVENTION

The present invention was created out of a need to be mobile while administering ice or heat to an injured joint, especially a synovial joint. An active person who suffers from a joint injury needs a treatment option that offers the ability to treat the injury while the person is mobile and donning clothing and footwear. The invention of the present disclosure is an apparatus that is unique in its ability to enable the administration ice, heat or both to the injured area while applying compression to the affected area without restricting motion and mobility of the injured joint of a patient wearing the apparatus. The present invention performs extremely reliably when worn with or without shoes in cases where a patient wears the apparatus in response to an injury of the ankle or Achilles region, and with or without clothing in other cases, such as when the injury is to a shoulder, hip, knee or elbow.

By offering patients the both unrestricted motion and the ability to wear clothing and footwear during therapy, an apparatus of the present invention significantly expands a patient's opportunity to get high quality rehabilitation through the application of ice and heat during periods of mobility. It is an object of the present invention to shorten recovery times for persons with joint injuries, especially synovial joint injuries, through use of an apparatus as described herein. Whether a patient is relaxing with feet up on the couch while watching television, wearing a suit and dress shoes in a meeting, or jumping rope on one leg, rehabilitation is taking place when an apparatus and method of the present invention is employed.

An apparatus of the present disclosure was developed to offer patients suffering from an injury a superior rehabilitation experience that has flexibility and versatility. An apparatus as described herein is unique in that is offers wearers the ability to get high quality ice and heat rehabilitation experience while at rest or on the go. An apparatus as described herein was developed not only as an icing and heating tool for synovial joint injury rehabilitation, but also as a new market alternative to common solutions such as wraps, stirrups and sleeves. An apparatus of the present invention was developed to perform at a high level in a variety of use scenarios.

Therefore, the invention of the present disclosure provides an adjustable compression apparatus for improving conditions of a joint, especially a synovial joint. An apparatus of the present disclosure is configured to provide resistance to normal movement of a joint, for example and not by way of limitation, a shoulder, elbow, hip, knee or ankle joint and surrounding areas, such as an area of an Achilles tendon. The invention of the present disclosure offers a treatment apparatus that does not hamper or impair normal movement of the joint to which the apparatus is applied. The present invention further provides for adjustable compression through adjustable securement means that allow the apparatus to be worn over shoes or clothing. The various embodiments described herein may include an adjustable support apparatus adaptable for one or more joints, such as and not by way of limitation, a knee joint, wrist joint, elbow joint, shoulder joint, ankle joint or hip joint.

DETAILED DESCRIPTION OF THE INVENTION

Figure 1:
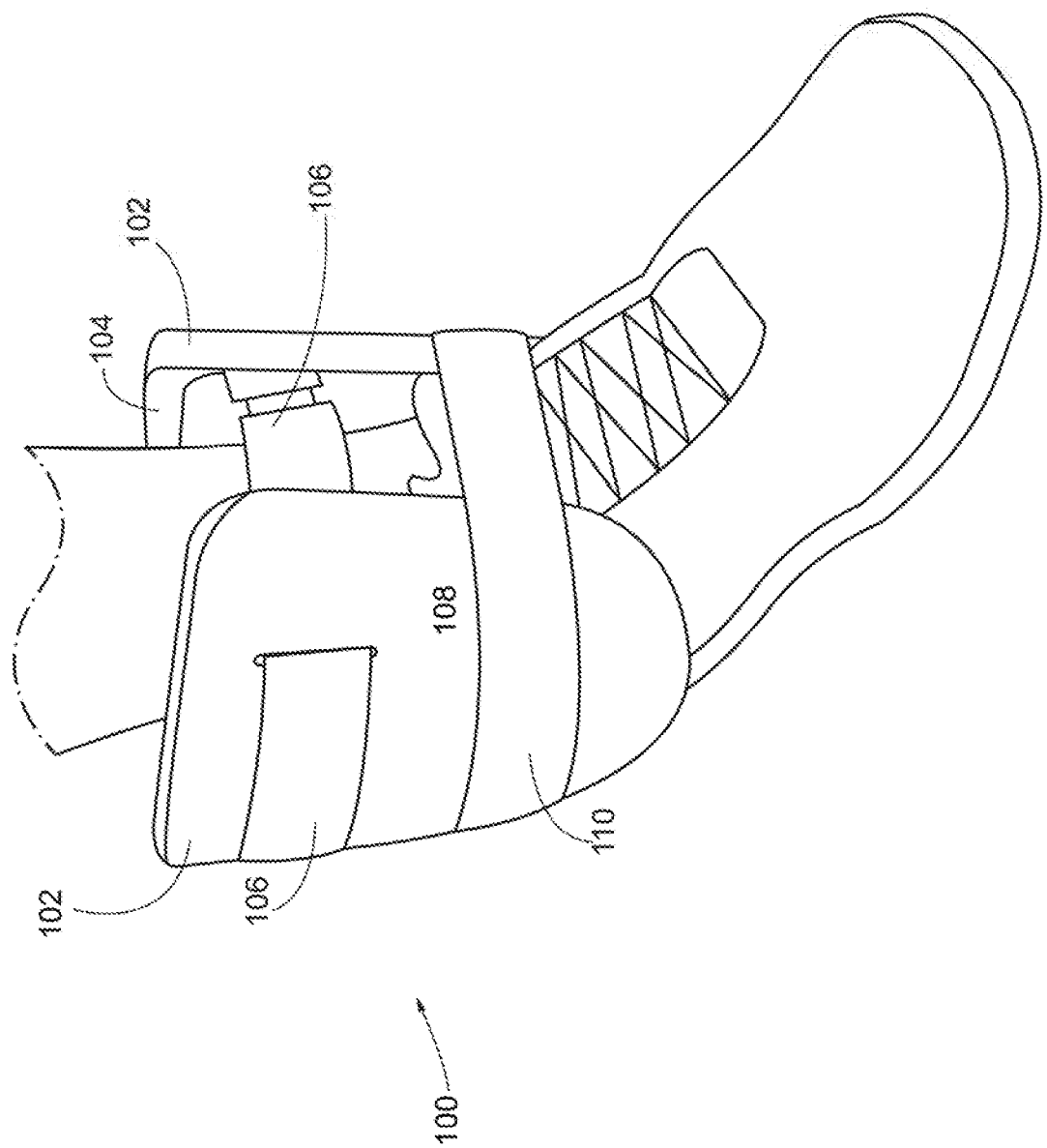
FIG. 1 shows a compression apparatus (assembled) configured for use in treating an ankle condition, according to one embodiment of the invention of the present disclosure.

Disclosed herein is an adjustable and flexible compression apparatus for use in treating pain, inflammation, and or other conditions of a joint and joint area of a body, particularly a synovial joint and surrounding area, and configured for physical and functional flexibility in that the compression apparatus is flexible and can be worn over clothing or footwear if necessary. The apparatus is generally suited for support of a major synovial joint such as an ankle, knee, wrist, elbow, shoulder or hip with minimal modifications. In certain embodiments, a key benefit over presently known compression or support means is the apparatus does not limit the user's mobility or require the user to forgo clothing or footwear. According to one embodiment of the present invention, the support is configured with heating or cooling means, such as compartments for securing temperature-control members such as inserts designed to apply hot or cold compression to the joint area; or alternatively, detachable temperature-control members configured to enable the apparatus to emit heat (to heat the joint and surrounding tissue) or absorb heat (to cool the joint area and surrounding tissue). In another embodiment, the joint support is additionally configured with an adjustable securement means allowing compression to be adjusted, such as but not limited to a strap or other wrap for fastening around the exterior of the apparatus when the apparatus is aligned in position over a wearer's joint so that additional pressure is applied to the joint by the apparatus.

In certain embodiments, a compression apparatus of the present disclosure comprises at least one flexible compression member, at least one temperature-control member; a first securement means; and a second securement means. In another embodiment the flexible compression members are conjoined. A compression apparatus as described herein is configured to provide a constant, adjustable compression around a joint of the wearer. A temperature-control means of the present invention may comprise one or both of a heating element and a cooling element.

In certain embodiments of the present disclosure, an apparatus of the present invention comprises at least one flexible compression member having joint facing side and an outward facing side; at least one securement means configured for adjusting compression to the joint area of a wearer; and a decorative feature affixed to the outward facing surface of a flexible compression member.

In certain embodiments of the present disclosure, an apparatus of the present invention comprises at least one flexible compression member having joint facing side and an outward facing side; at least one securement means configured for adjusting compression to the joint area of a wearer; and a visual display such as a screen (such as but not limited to a light-emitting diode (LED) screen) that is flexible to allow for compatibility with use of an apparatus as described herein. A screen as referred to herein may be temporarily affixed to or permanently incorporated into the exterior of a compression member of an apparatus for the purpose of displaying digital data, digital effects, images and text messages, for example and not by way of limitation. In certain embodiments, images, messages, information and data presented on the display can be either locally saved, uploaded to the device, wirelessly cast, or streamed to the device.

In certain embodiments, equipment or electronics either permanently incorporated or temporarily affixed to an apparatus of the present disclosure for the purpose of originating or capturing data and information on or from the user (or user environment) and either saving locally or casting or streaming the data and information out to another device or data hub for tracking, monitoring, trending, etc. Such data and information may include, for example, pedometer data, usage time statistics and average temperature.

It is anticipated that there may be scenarios where physicians, users, and others may want local or remote access to data gathered by an apparatus of the present invention. Generally, in scenarios where data and information is wirelessly streamed or cast to a device certain electronic hardware and software that support data transmission are incorporated into an apparatus according to certain embodiments of the present invention, such as short-wave ultra high frequency (UHF) according to standards such as that developed by the Bluetooth Special Interest Group.

In certain embodiments of a compression apparatus as described herein, an apparatus may further comprise one or more devices that capture elevation angles and other general orientation information that may be useful to obtain in connection with use of the apparatus. As referred to herein, elevation (or orientation) angles are angles of elevation of a joint being treated as described herein relative to a horizontal axis. Examples of devices suitable for measuring elevation angles include: locally affixed ball bearing level indicators; locally affixed liquid equilibrium indicators ("levels"); gyroscope device technologies; and any other device that identifies, indicates, or captures elevation or orientation angles of an apparatus to which such a device is affixed. A benefit of temporarily or permanently affixing a device suitable for measurement and tracking of elevation angles during use of an apparatus as described herein is that R.I.C.E. (Rest, Ice, Compression, and Elevation) is very important with regard to joint rehabilitation. Such devices can be temporarily affixed to or permanently incorporated within a compression apparatus as described herein, for example but not by way of limitation, at the storage compartments for one or more temperature control members (referenced above) for the purpose of indicating or identifying the angle by which the user is orienting an injured area while using an apparatus as described herein for rehabilitation.

Scenarios are anticipated where physicians, users, and others may want to view, monitor, and track with greater precision the angle of elevation being applied to an injured area during rehabilitation with an apparatus as described herein. This will give physician, users, or others the ability to process direct information regarding the angle at which the injured area is elevated during rehabilitation (e.g., 25 degrees during use versus 65 degrees elevated during rehab, etc.).

In other embodiments of the present invention, an apparatus as described herein may further comprise devices or indicators that identify, capture and transmit real-time temperature details. These devices can be temporarily affixed to or permanently incorporated within a storage compartment as described above, for example and not by way of limitation, for the purpose of monitoring temperatures that the user may be experiencing during use of a compression apparatus of the present disclosure.

Also disclosed herein is a method of treating pain, inflammation, or other injury to a joint of a person, especially a synovial joint is also disclosed, the method comprising: aligning one or more of a compression apparatus having a joint facing side and an outward facing side on either side of an injured joint; tightening a first securement means by bringing its ends together and securing it at an appropriate tightness to provide the desired compression against the joint area, wherein the first securement means is connected to the one or more flexible compression members via lacing through the same and secured in an under-weave arrangement between the compression members and positioned near or around the joint; and securing a second securement means around the outer facing side of the one or more flexible compression members aligned around an injured joint within the lower half of the flexible compression members, wherein the second securement means is secured in an over-weave arrangement to provide appropriate compression around a joint area to provide the desired compression against the injured joint.

Reference is now made to the accompanying drawings, wherein are shown various embodiments of the invention. In the various embodiments shown in the drawings, one or more flexible compression members comprise a joint facing side to abut and cover at least a portion of a joint area. For example, one or more flexible compression members may be configured to cover and apply compression to the joint area. In one embodiment, the one or more flexible compression members are held in position around the joint of the wearer by one or more securement means. In another embodiment, one or more flexible compression members and one or more securement means are configured to provide compression to the joint area, adjustable depending on the tautness of the one or more securement means when the apparatus is fully assembled and fastened around the joint area.

FIG. 1 shows a compression apparatus (assembled) 100 comprising a pair of joint one or more flexible compression members 102, contoured in shape to fit over an ankle area of a wearer (shown in the figure as positioned over the inner and outer area of an ankle region of the wearer). One or more flexible compression members 102 have a joint facing side 104. One or more flexible compression members 102 are held in position around the joint of a wearer by a first securement means 106 (shown in FIG. 1 as a strap). The first securement means 106 is positioned within the top half of the one or more flexible compression members and interwoven within the one or more flexible compression members 102 via one or more openings 108 positioned on the one or more flexible compression members 102 within the top half of the one or more flexible compression members. Openings 108 are vertically oriented and arranged in a horizontal row. The first securement means 106 is woven or laced through an opening 108, thereby traversing the one or more flexible compression members 102 at openings 108 so that a portion of a strap resides on the outward facing side of the one or more flexible compression members, and a portion of the strap resides on the joint facing side of the one or more flexible compression members. The ends of the first securement means 106 are secured to each other, forming a closure, in an area within the lower half of the one or more flexible compression members, in what is termed an "under-weave" arrangement.

The one or more flexible compression members 102 align on either side of the joint, shown in the figure as fitting around the left side and right side of the ankle joint. In one embodiment, the first securement means 106 is a strap (preferably an elasticized strap), and configured with closure means, such as snaps, buttons, magnetic fasteners, hook and loop fasteners, ties, or other suitable means of securing the strap at a particular length around the ankle that holds the flexible compression members in position. An apparatus 100 is configured with a second securement means 110 (shown in the figure as a strap wrapped around the outer surface of one or more flexible compression members 102). The first securement means 106 and second securement means 110 allow for compression of the one or more flexible compression members around the joint area. The second securement means 110 wraps on the outer side of the each of the one or more flexible compression members, in what is termed an "over-weave" arrangement, for compression adjustment and ease of assembly and removal. In FIG. 1, a second securement means 110 is shown as a strap. In one embodiment, the strap is an elasticized strap, and configured with closure means, such as snaps, buttons, magnetic fasteners, hook and loop fasteners, ties, or other suitable means of securing the strap around the assembled flexible compression members at a tension to provide compression against the joint area.

Figure 2:
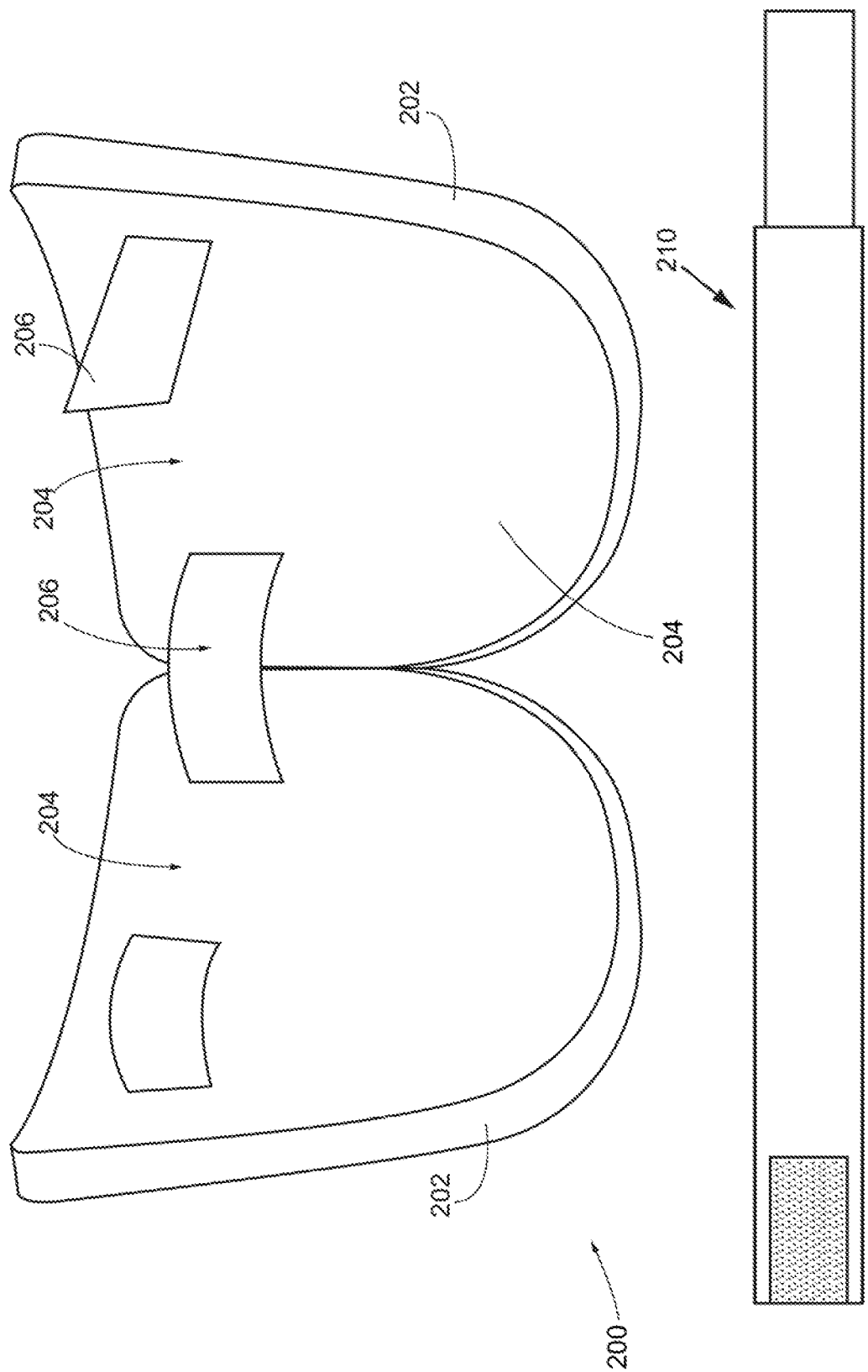
FIG. 2 shows a compression apparatus (unassembled) configured for use in treating an ankle condition, according to one embodiment of the invention of the present disclosure.

FIG. 2 shows a compression apparatus (unassembled) 200 comprising a pair of flexible compression members 202, each having a joint facing side 204, wherein the flexible compression members 202 are configured with a plurality of openings 208 through which first securement means 206 is interwoven. The first securement means 206 is shown in FIG. 2 as a strap. To assemble the apparatus 200, flexible compression members 202 are aligned on either side of an ankle joint of a wearer, and strap 206 is secured by bringing the ends together and securing the strap at a length the keeps the flexible compression members 202 aligned securely at the joint. Also shown in FIG. 2 is second securement means 210, shown in the figure as a strap configured with hook and loop fasteners at either end of the strap.

Figure 3:
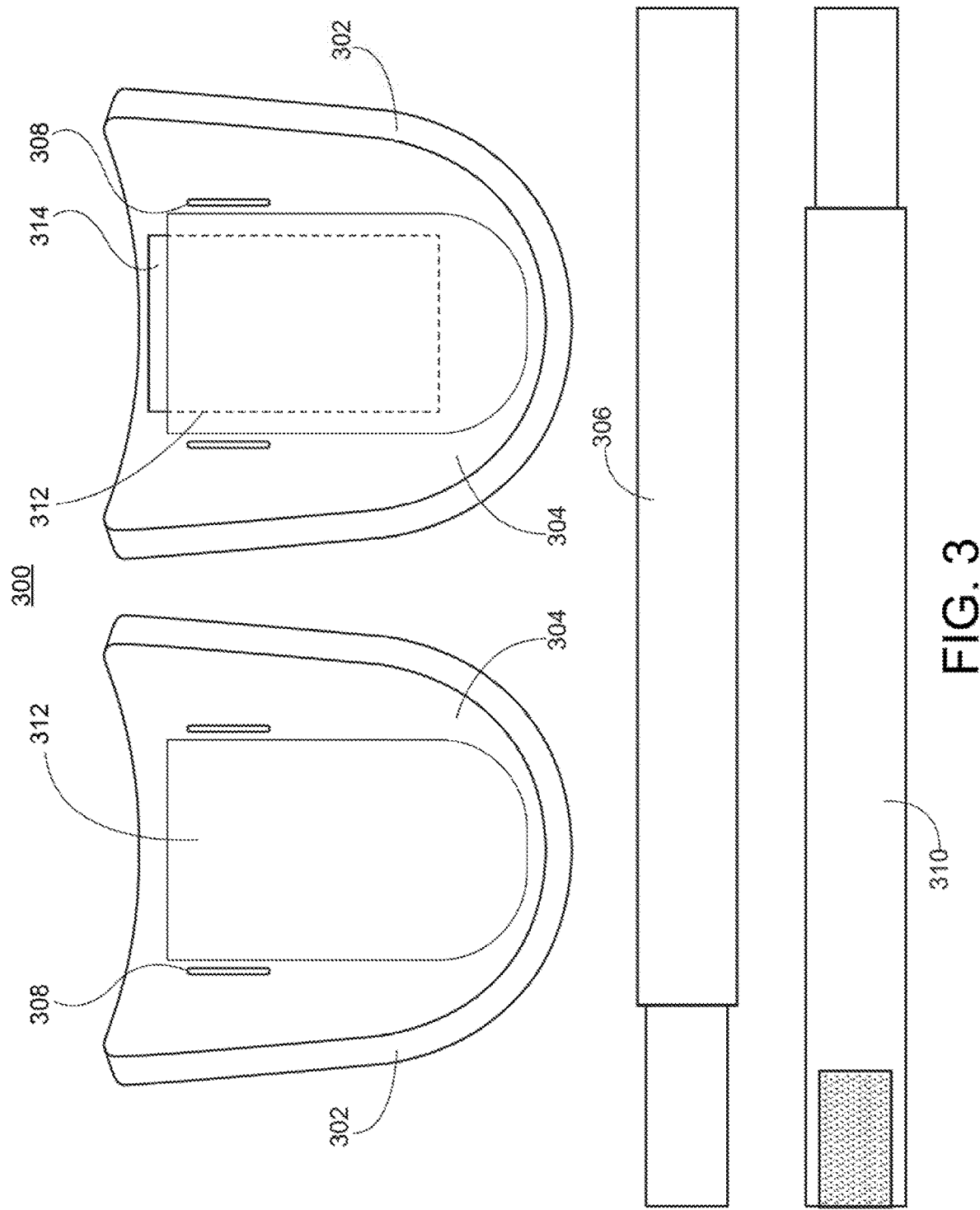
FIG. 3 shows a compression apparatus (unassembled) configured for use in treating an ankle condition, according to one embodiment of the invention of the present disclosure, further configured with storage compartments for one or more temperature control members.

Shown in FIG. 3 is a compression apparatus (unassembled) 300 comprising a pair of flexible compression members 302 configured with an inner storage compartment 312 on the joint facing side 304 of the flexible compression members 302 for storage of a heating or cooling element 314. Also shown on the flexible compression members 302 are openings 308 for weaving of first securement means 306. A second securement means 310 is also shown.

Figure 4:
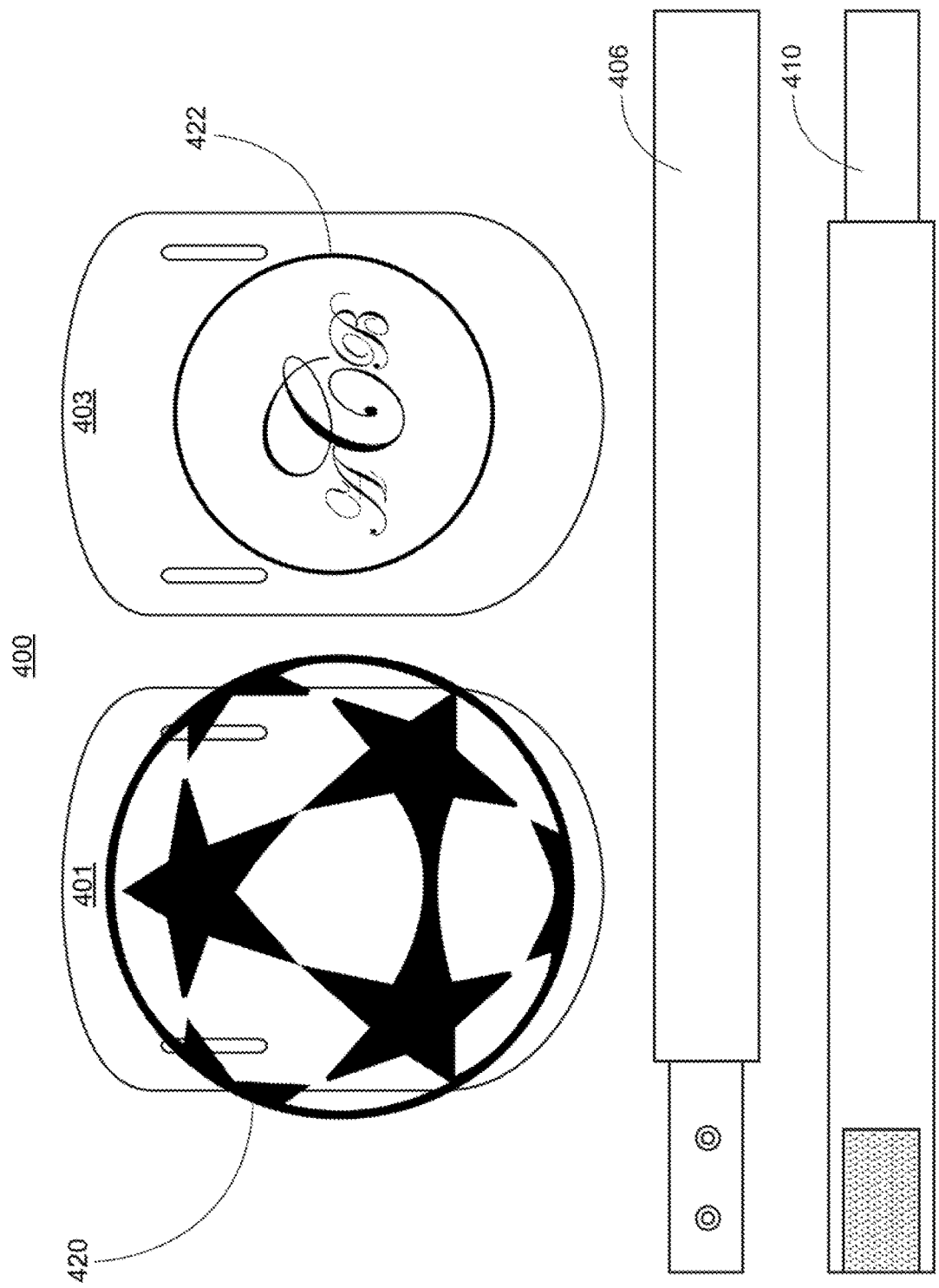
FIG. 4 shows a compression apparatus (unassembled) configured for use in treating an ankle condition, according to one embodiment of the invention of the present disclosure, further with a decorative attachment.

FIG. 4 shows a compression apparatus (unassembled) 400 comprising a first flexible compression member 401 configured with a decorative feature 420 attached to the outer facing surface of the flexible compression member 401. In this embodiment, a decorative feature 420 is shown in the figure as an overlay configured with an illustration of a soccer ball. In one embodiment, the decorative feature is essentially flat, or may be a 2- or 3-dimensional feature that attaches to an outer surface of the flexible compression member or wraps around the flexible compression member to which the feature attaches. A decorative feature may be of natural or synthetic materials, such as nylon, plastic, leather, and the like or any combination thereof. Also shown is a flexible compression member 403 configured with a decorative feature 422, shown here as a monogram disposed on the surface of the flexible compression member 403 on the outward facing side. A decorative feature 422 may be attached by various attachment means, including but not limited to hook and loop fasteners, snaps, magnets, tape, glue, adhesives and the like. A decorative feature may also be embossed, engraved, reversibly attached or permanently attached to flexible compression member 403. Also shown in FIG. 4 are securement means comprising straps configured with closure means, such as snaps shown on a strap 406 and hook and loop fasteners on the strap 410.

Figure 5A:
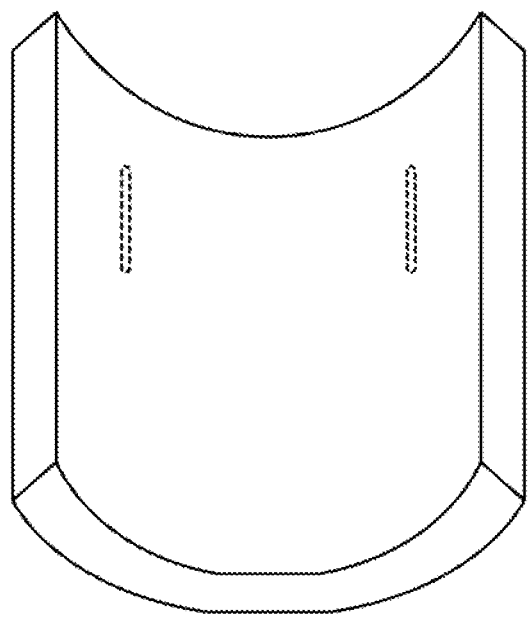
FIGS. 5A-5K show flexible compression members of compression apparatuses according to various embodiments of the invention of the present disclosure, configured with slots for receiving a securement means for under-weaving and shaped to be used to treat various parts of a body of a user.
Figure 5B:
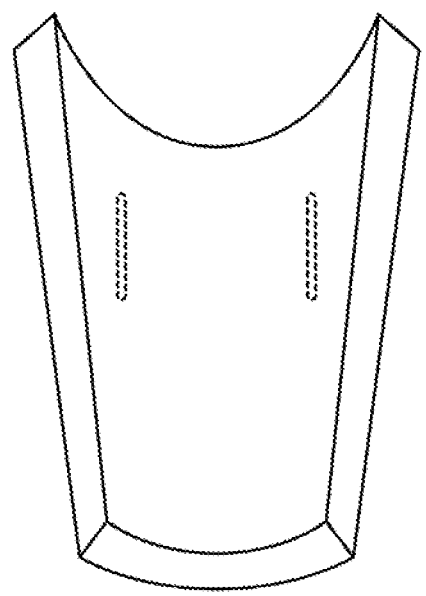

FIGS. 5A-5K illustrate various shapes that are possible for a flexible compression member of an apparatus as described herein, as one of ordinary skill in the art will appreciate. For example, and not by way of limitation, a flexible compression member according to the present disclosure may be essentially a concave rectangle as shown in FIG. 5A, optionally configured with slots for a securement means such as a strap to weave through in an under-weave arrangement. Alternatively, and not by way of limitation, a flexible compression member according to the present disclosure may be in the form of a concave trapezoid as shown in FIG. 5B, optionally configured with slots for a securement means such as a strap to weave through in an under-weave arrangement.

Figure 5C:
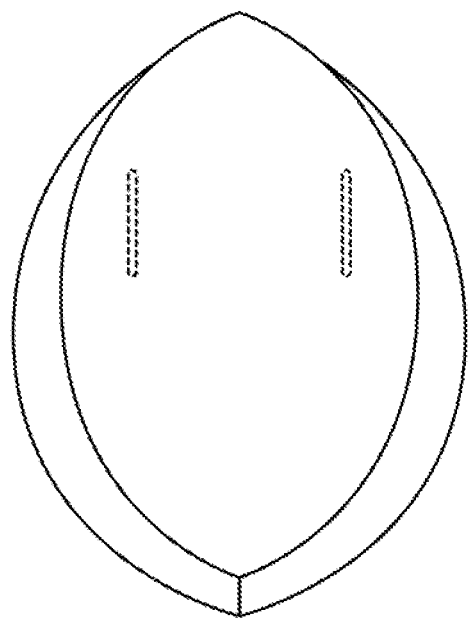
Figure 5D:
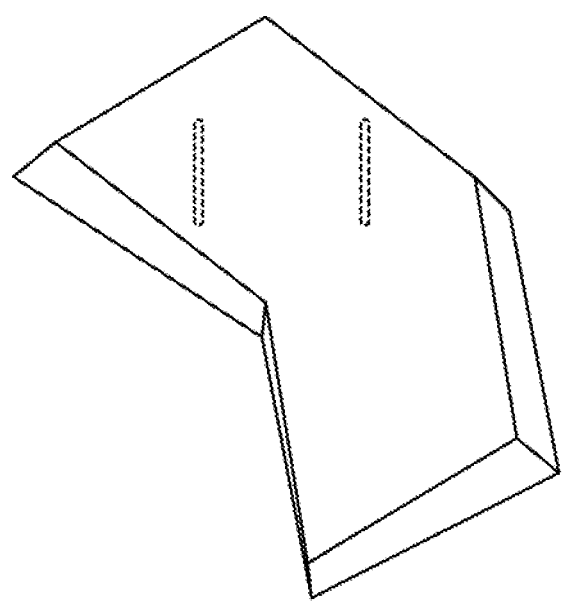

Alternatively, and not by way of limitation, a flexible compression member according to the present disclosure may be in the form of a concave oval or ellipse as shown in FIG. 5C, optionally configured with slots for a securement means such as a strap to weave through in an under-weave arrangement. Alternatively, and not by way of limitation, a flexible compression member according to the present disclosure may comprise an angled concavity as shown in FIG. 5D, optionally configured with slots for a securement means such as a strap to weave through in an under-weave arrangement, such as might align, for example, on the inside or outside of a bent knee or elbow.

Figure 5E:
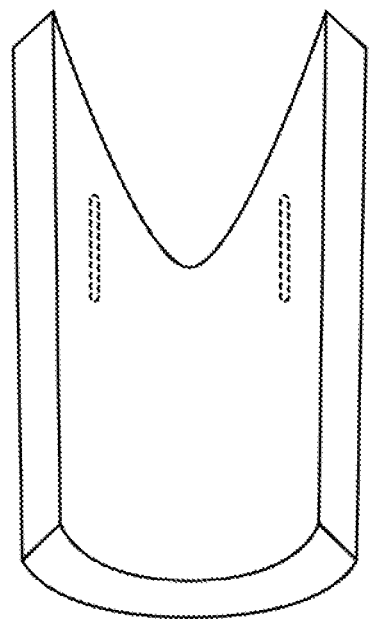
Figure 5F:
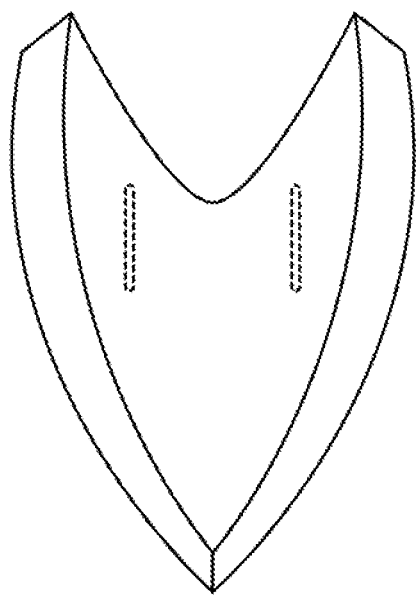

Alternatively, and not by way of limitation, a flexible compression member according to the present disclosure may be in the form of a concave rectangle or ellipse further comprising a cutout as shown in FIGS. 5E and 5F, optionally configured with slots for a securement means such as a strap to weave through in an under-weave arrangement. The cutout might allow for treatment of an area, for example, adjacent to a knee or elbow without covering the knee or elbow.

Figure 5G:
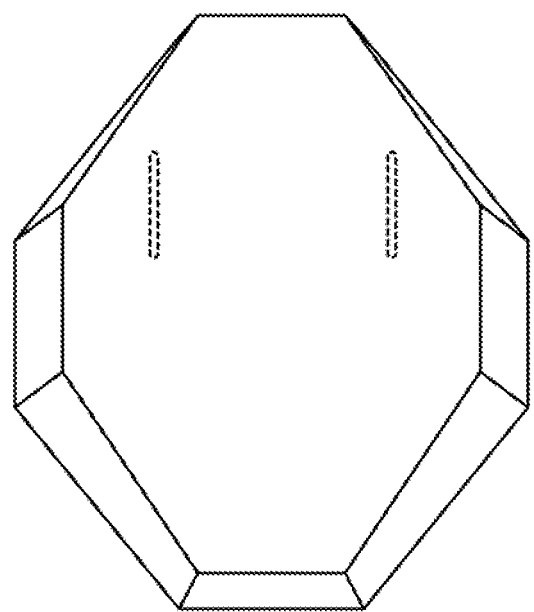
Figure 5H:
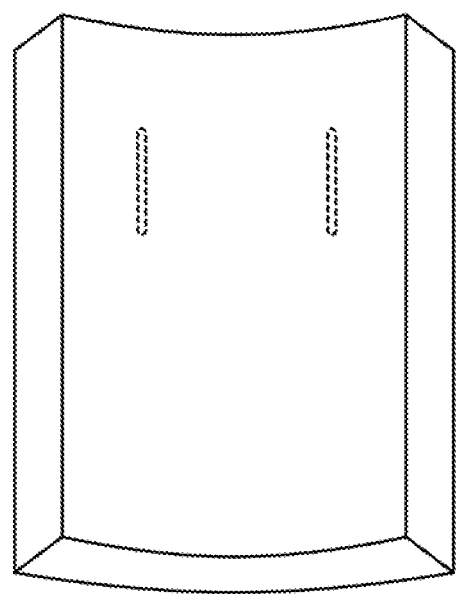

Alternatively, and not by way of limitation, a flexible compression member according to the present disclosure may be in the form of a concave octagon as shown in FIG. 5G, optionally configured with slots for a securement means such as a strap to weave through in an under-weave arrangement. Alternatively, and not by way of limitation, a flexible compression member according to the present disclosure may be in the form of a concave rectangle similar to that of FIG. 5A but narrower, as shown in FIG. 5H, optionally configured with slots for a securement means such as a strap to weave through in an under-weave arrangement.

Figure 5I:
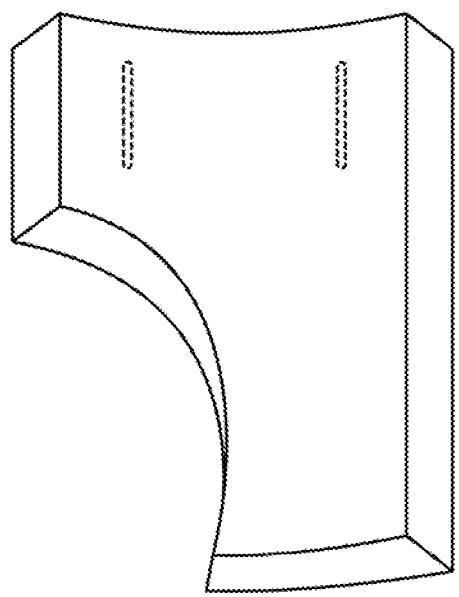
Figure 5J:
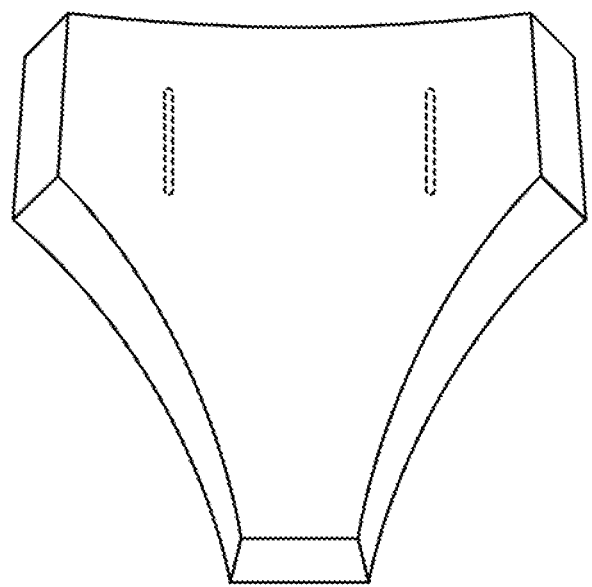

Alternatively, and not by way of limitation, a flexible compression member according to the present disclosure may be in the form of a concave rectangle with a portion cut out, as shown in FIG. 5I, optionally configured with slots for a securement means such as a strap to weave through in an under-weave arrangement. Alternatively, and not by way of limitation, a flexible compression member according to the present disclosure may be in the form of a concave member designed to fit around a groin area of a user, as shown in FIG. 5J, optionally configured with slots for a securement means such as a strap to weave through in an under-weave arrangement.

Figure 5K:
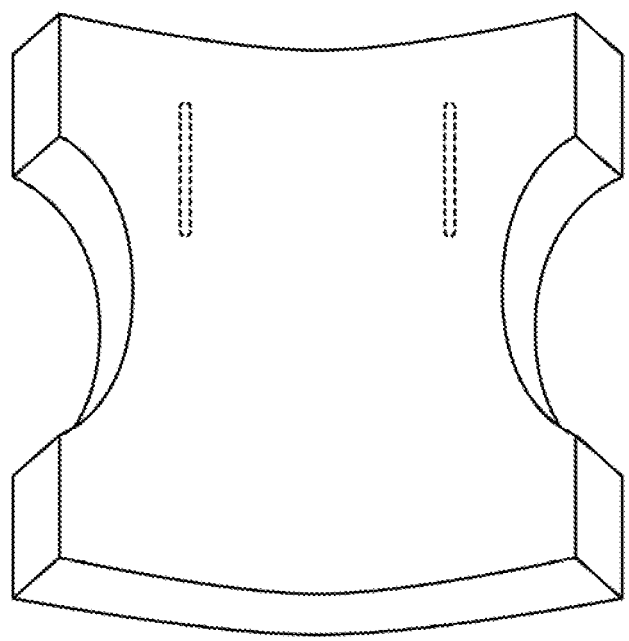

Alternatively, and not by way of limitation, a flexible compression member according to the present disclosure may be in the form of a concave member designed to strap around a lower back of a user, such as is depicted in FIG. 5K, optionally configured with slots for a securement means such as a strap to weave through in an under-weave arrangement.

Figure 6B:
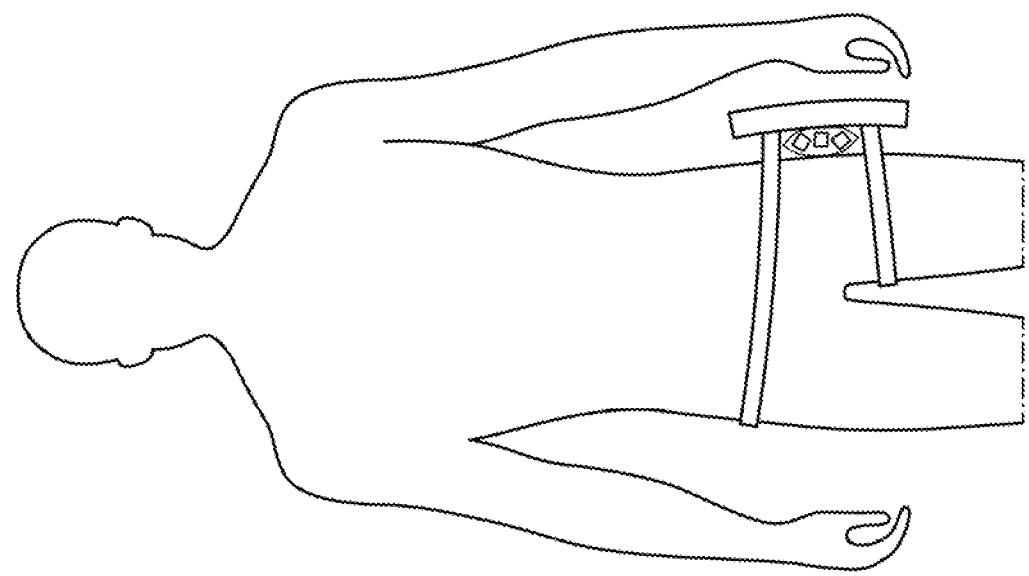
FIG. 6B shows a compression apparatus according to one embodiment of the invention of the present disclosure, configured with securement means for treating a hip of a user.
Figure 6A:
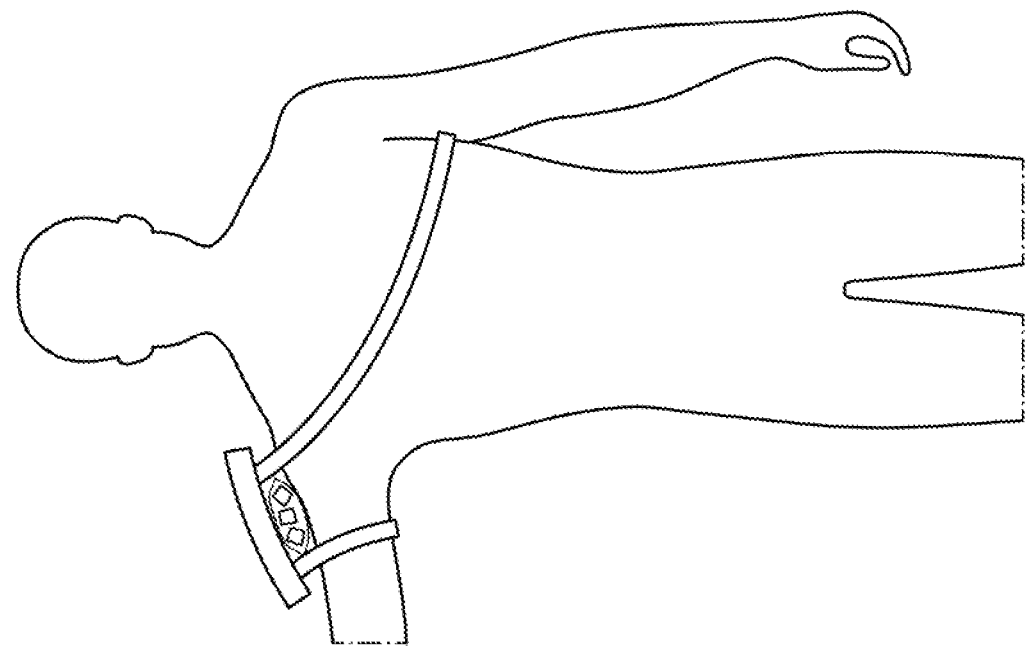
FIG. 6A shows a compression apparatus according to one embodiment of the invention of the present disclosure, configured with securement means for treating a shoulder of a user.

In certain embodiments such as those shown in FIGS. 6A and 6B, securement means may be of varying lengths to allow for securement of a flexible compression member above a shoulder or on the outside of a hip of a user, respectively. In the embodiments shown in FIGS. 6A and 6B, a flexible compression member may be configured with two sets of two slots, such that two under-weave arrangements may be achieved to treat areas such as those pictured, for example and not by way of limitation.

Figure 7:
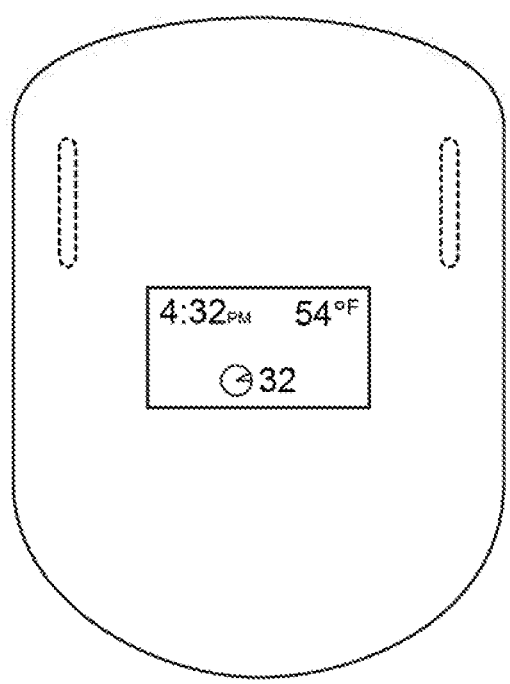
FIG. 7 shows a compression apparatus according to one embodiment of the invention of the present disclosure, configured with a display screen indicating time, temperature and elevation angle when in use.

In an embodiment as shown in FIG. 7, a flexible compression member as described herein may comprise a visual display of use information associated with a compression apparatus of the present invention. As one of ordinary skill in the art will appreciate, a user of the invention of the present disclosure may wish to track use data such as but not limited to the length of time a compression apparatus as described herein has been in use, its temperature and an angle of elevation or orientation of a joint being treated using an apparatus as described herein. This will enable users to achieve greater efficiency of use and follow recommendations such as those that might be made by a physician in terms of how long a joint should be treated, whether it should be elevated and at what temperature.

In one embodiment, the one or more flexible compression members are made of natural or synthetic materials and may be of one or more layers of materials of varying thickness. In one embodiment, materials may be an oblong piece of one or more of a durable, flexible, impermeable, resilient, natural or synthetic material, such as chemically-resistant plastics, such as polyethylene or polypropylene, or foams such as polyurethane foam. In one embodiment, meant to be illustrative and not exhaustive, one or more flexible compression members are generally of a size ranging from five to seven inches by three to five inches and may range in thickness from about 0.25 to 0.5 inches. Various other sizes for flexible compression members are contemplated, such as to match pediatric measurements, which may require smaller dimensions. Likewise, depending on the size of the wearer, or the joint area to be supported, flexible compression members may be configured with dimensions of greater than seven inches by greater than five inches. The one or more flexible compression members may be of equal dimensions, or alternatively, of different sizes and thicknesses. The one or more flexible compression members may be of varying shapes and sizes and may be configured with a contoured shape, such as forming a concavity on the joint facing side.

In one embodiment, one or more flexible compression members are configured with a detachable decorative attachment on the outer facing side of the one or more flexible compression members. Decorative attachments may be of various forms and made of various materials. In one embodiment, a decorative attachment is a decorative layer, such as a layer of material comprising an image or design. The decorative layer may be of varying thickness or size and may cover all or a portion of the one or more flexible compression members. In another embodiment, the decorative layer may be permanently affixed to the flexible compression member or may be reversibly attached by engagement or disengagement of attachment means on the one or more flexible compression members and decorative layer. Attachment means include snaps, buttons, magnetic fasteners, hook and loop fasteners and the like.

In one embodiment, securements means may be comprised of one or more of an elastic or other straps configured with closure means comprising hook and loop fasteners, hook and eye closures, snaps, zippers, laces, adhesives such as tape, and any other suitable means of securing the strap in position on the assembled joint apparatus. In one embodiment, the strap is of a length ranging in inches from 11 inches to 13 inches, although the length of the strap depends on the wearer. In one embodiment, for pediatric users a shorter strap may be desired, whereas for a larger adult a longer strap may be desired. In another embodiment, the strap is of a width ranging in inches from 0.25 inches to 1.5 inches.

In one embodiment, temperature control members are configured for releasing heat or absorbing heat. In one embodiment, the temperature-control members may be one or more of a heating insert, such as inserts containing heat-releasing materials, or a cooling insert, such as an ice pack, or gel pack containing cooling materials, or other suitable heating or cooling agents.

In one embodiment, the one or more flexible compression members are configured with inner compartments for holding and securing the inserts, such as pockets on the joint facing surface of the one or more flexible compression members. In another embodiment, the temperature-control members are reversibly attached to the ankle facing surface of the one or more flexible compression members by attachment means, such as snaps, zippers, hook and loop fasteners, adhesives, such as tape, or other suitable means of reversibly attaching the temperature control members to the one or more flexible compression members. In one embodiment, the temperature-control members are single-use, although in another embodiment, the temperature are reusable.

In one embodiment, a first securement means is configured as a strap with a woven configuration with the one or more flexible compression members for the purpose of maintaining compression. In one embodiment, a first securement means is configured as an under-weave assembly positioned near the top of one or more flexible compression members. In another embodiment, the second securement means is configured as an over-weave assembly positioned lower on the one or more flexible compression members. The arrangement of securement means as an under-weave or over-weave are for convenience as well as utility. The under-weave or over-weave arrangement of the securement means with the one or more flexible compression members provides for greater compression efficiency, yet still provides ease of use for the wearer. In one embodiment, the second securement means is configured (in the assembled position) along the outer surface (over-weave) of the one or more flexible compression members, for maximum control over compression of the one or more flexible compression members against the joint area, and for comfort precision and adjustment.

In another embodiment, the inter-laced pattern of first securement means with one or more flexible compression members is dependent, in part, by the number of openings positioned on the one or more flexible compression members. In one embodiment, one or more flexible compression members are configured with one or more, preferably from two up to four, openings per compression member, with the openings configured as vertical slants or openings positioned linearly (in a row) along the upper portion of the one or more flexible compression members. The openings are of a dimension commensurate with the width and thickness of the first securement means (strap). In another embodiment, one or more vertical openings may also be positioned linearly along the lower portion of one or more flexible compression members for interlacing of the second securement means.

In one embodiment, a compression apparatus may be used in combination with an ice-pack, such as a bag of ice or a cool gel pack, by placing the ice-pack or other cold treatment in the space between the flexible compression member and the joint area of the wearer. The securement means are adjustable so that depending on the amount of ice needed to effectively treat an affected area of the joint is held in position by at least a portion of the one or more flexible compression members, with a portion of the ice pack or cool gel pack abutting the joint facing side of at least one of the one or more flexible compression members.

It will be clear to a person skilled in the art that features described in relation to any of the embodiments described above can be applicable interchangeably between the different embodiments. The embodiments described above are examples to illustrate various features of the invention, and they are not exhaustive or exclusive.

Throughout the description and claims of this specification, the words "comprise" and "contain" and variations of them mean "including but not limited to", and they are not intended to (and do not) exclude other additives, components, materials or steps. Throughout, the singular encompasses the plural unless the context otherwise requires. In particular, where an indefinite article is used, the specification is to be understood as contemplating plurality as well as singularity, unless the context requires otherwise.

Features, materials and characteristics described in conjunction with a particular aspect, embodiment or example of the invention are to be understood to be applicable to any other aspect, embodiment or example described herein unless incompatible therewith. The invention is not restricted to the details of any foregoing embodiments. The invention extends to any feature or combination of the features disclosed in this specification (including any accompanying claims, abstract and drawings), or to any step or steps of any method or process so disclosed.

What is claimed is:

1. A compression apparatus for treating a synovial joint, the apparatus consisting essentially of at least one concave flexible compression member configured with at least one pair of slots and at least one adjustable length strap woven through the at least one pair of slots;
   wherein the at least one concave flexible compression member is configured in a shape selected from the group consisting of a rectangle, a trapezoid, an ellipse, an octagon and a square; and
   wherein a portion of the shape is cut out to accommodate a gel pack selected from the group consisting of a heat pack and a cold pack;
   the compression apparatus further comprising at least one visual information display in network communication with at least one remote computing device, wherein a user of the remote computing device can see the information that is displayed on the visual information display;
   wherein information displayed on the visual information display is selected from the group consisting of time, temperature and elevation angle information.

2. The compression apparatus of claim 1, wherein the adjustable length strap may configured to cause the concave flexible compression member to provide an increased level of compression to the synovial joint when the strap is tightened.

3. A method of treating a condition of a synovial joint of a user, the method comprising:
   aligning the at least one concave flexible compression member such that its concavity surrounds the synovial joint or an adjacent area;
   securing a first strap by bringing ends together and securing at an appropriate tightness to provide compression against the synovial joint, wherein the first strap is connected to the at least one concave flexible compression member via weaving through the at least one pair of slots and securing in an under-weave arrangement; and securing a second strap around the outward facing side of the at least one concave flexible compression member, wherein the second strap is secured in an over-weave arrangement to provide appropriate compression to the synovial joint;

wherein the at least one concave flexible compression member further comprises at least one gel pack selected from the group consisting of a heat pack and a cold pack and at least one visual information display;

wherein information displayed on the visual information display is selected from the group consisting of time, temperature and elevation angle information;

reading information displayed on the visual information display and adjusting at least one parameter of treatment of the synovial joint based on the information displayed; and transmitting the information displayed on the visual information display to a remote computing device.

4. The method of claim 3, wherein the at least one concave flexible compression member is two concave flexible compression members secured to opposite sides of the synovial joint.

\* \* \* \* \*